US006455547B1

(12) United States Patent
Kis

(10) Patent No.: US 6,455,547 B1
(45) Date of Patent: Sep. 24, 2002

(54) METHOD FOR TREATING PHARMACEUTICAL COMPOSITIONS

(75) Inventor: Gyorgy Lajos Kis, Triboltingen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/033,285

(22) Filed: Dec. 21, 2001

Related U.S. Application Data

(63) Continuation of application No. 09/627,799, filed on Jul. 31, 2000, which is a continuation of application No. PCT/EP99/02221, filed on Mar. 31, 1999.

(30) Foreign Application Priority Data

Apr. 2, 1998 (EP) .............................................. 98106046

(51) Int. Cl.$^7$ ............................................. A61K 31/445
(52) U.S. Cl. ...................................... 514/324; 514/912
(58) Field of Search ................................. 514/324, 912

(56) References Cited

U.S. PATENT DOCUMENTS

| 3,966,905 A | 6/1976 | Nite .............................. 424/80 |
| 4,959,208 A | 9/1990 | Chakrabarti et al. .......... 424/78 |

FOREIGN PATENT DOCUMENTS

| EP | 0 827 741 A2 | 3/1998 |

OTHER PUBLICATIONS

Patent Abstracts of Japan, Kenichi, JP 08165240, Jun. 25, 1996, "Ketotifen–Containing Percutaneously Administering Preparation,".

European Search Report (EP 98 10 6046, Sep. 14, 1998).
PCT International Search Report (PCT/EP99/02221, Mar. 31, 1999).
Fujita et al., Clinical Efficacy and Optimal Concentration of Ketotifen Ophthalmic on Allergic Conjunctivitis and Vernal Conjunctivitis, J. Clinical Therapeutic and Medicines (Japan), 5(4):709–721, 1989.
Kawasaki et al., Iyakuhin Kenkyu, vol. 19(5), "Eye Irritation Study on Ketotifen Fumarate–Containing Eye Drops in Rabbits (I) Eye Irritability on Single or Frequent Topical Instillation", pp. 821–826, (1988) [English translation].
Kawasaki et al., Iyakuhin Kenkyu, vol. 19(5), "Eye Irritation Study on Ketotifen Fumarate–Containing Eye Drops in Rabbits (II) Eye Irritability on Successive Four–Week or Thirteen Week Instillations", pp. 827–838, (1988) [English translation].
Mikuni et al., Rinsho Iyaku [Journal of Clinical Therapeutic and Medicines], vol. 4(12), "Evaluation of Ketotifen Ophthalmic Solution on Efficacy and Safety on Allergic Conjunctivitis and Vernal Conjunctivitis—Result on Multiclinic Open Trial—", pp. 2371–2383, (1988) [English translation].
Mikuni et al., Ringan [Japanese Journal of Clinical Ophthalmology], vol. 36(6), "Quantitative Therapeutic Efficacy of Ketotifen Eye Drops for Allergic Conjunctivitis", pp. 573–576, (1982) [English translation].
Mikuni et al., Tokai J Exp Clin Med., vol. 9, No. 1, "A Quantitative Tear Fluids Determination of Therapeutic Efficacy for Allergic Conjunctivitis", pp. 35–41, (1984).
Nakayasu et al., Safety of Ketotifen Ophthalmic Solution on Ocular External and Front Region, J. Clinical Therapeutic and Medicines (Japan), 4(12):2357–2369, 1989.

*Primary Examiner*—Zohreh Fay
(74) *Attorney, Agent, or Firm*—David E. Wildman

(57) ABSTRACT

The invention provides stabilized ophthalmic compositions and methods for stabilizing ophthalmic compositions.

9 Claims, No Drawings

METHOD FOR TREATING PHARMACEUTICAL COMPOSITIONS

This application is a continuation application of Ser. No. 09/627,799 filed on Jul. 31, 2000 which is pending which is a continuation of PCT/EP99/02221 filed Mar. 31, 1999.

The present invention describes in particular a method for stabilizing a pharmaceutical composition by contacting said composition with a polymeric material comprising an antioxidant.

There exists a need to stabilize pharmaceutical compositions, in particular aqueous pharmaceutical compositions and in particular aqueous eye drops, such that they are stable against decomposition caused by heat, light and/or oxygen exposure.

The problem has been solved in accordance to the main claim, namely in particular by the use of a plastic bottle, wherein an antioxidant is comprised. The advantage of such a stabilization consists in the possibility to omit an additional antioxidant and/or a stabilizer otherwise needed in such pharmaceutical compositions. Therefore, such pharmaceutical compositions usually exhibit an enhanced tolerability as compared to ordinarily stabilized compositions, since the antioxidant is not administered to the organism in need of such a pharmaceutical composition.

Consequently, an object of the present invention is a method of stabilizing a pharmaceutical composition in particular in accordance to the main claim, e.g. by use of a plastic bottle comprising an antioxidant.

Within the present invention stabilization relates to the stability of the pharmaceutical composition in total and in particular to the stability of the active ingredient itself when exposed to storage, oxygen and/or air (oxygen radicals), light (UV) and/or heat (e.g. sterilization step at 121° C.). Heat sterilization will equally refer to autoclavation.

The term polymeric material relates to a polymer which is preferably insoluble in the liquid pharmaceutical composition of the present invention and which polymeric material may further be in the form of a random mold. Examples of molds are in particular a pellet, a bead, a rod, a bar, a sheet, a tube, or a vessel and more preferably a bottle. A preferred polymeric material comprises or consists of polyethylene (PE), polypropylene (PP) and/or mixtures thereof.

Consequently, the term plastic bottle relates in particular to a polyethylene (PE) and/or a polypropylene (PP) bottle. These may optionally contain further auxiliaries such as a light absorbing material e.g. titanium dioxide, a color pigment, a UV-absorber and/or the like.

An antioxidant within the terms of the present invention is understood to be a compound selected from the group consisting of 2,2',2",6,6',6"-Hexa-(1,1-dimethylethyl)4,4', 4"-[(2,4,6-trimethyl-1,3,5-benzenetriyl)-trismethylene]-triphenol (Irganox 1330), 1,3,5tris[3,5-di(1,1-dimethylethyl) 4-hydroxybenzyl]-1H,3H,5H-1,3,5-triazine-2,4,6-trione, pentaerythrityl tetrakis[3-[3,5-di(1,1-dimethylethyl)-4-hydroxyphenyl]-propionate], octadecyl-3-[3,5-di(1,1-dimethylethyl)-4-hydroxyphenyl]-propionate, tris[2,4-di(1, 1-dimethylethyl)-phenyl]-phosphite, 2,2'-di(octadecyloxy)-5,5'-spirobi(1,3,2-dioxaphosphorinane), dioctadecyl disulphide, didodecyl-3,3'-thiodipropionate, dioctadecyl-3, 3'-thiodipropionate, butylhydroxytoluene, ethylene bis[3,3-di[3-(1,1-dimethylethyl)-4-hydroxyphenyl]butyrate] and mixtures thereof. A preferred antioxidant is Irganox 1330.

The amount of antioxidant comprised in the polymeric material is typically in the range of the recommendations of the European Pharmacopoeia and is typically from 0.05–1.0 wt. %, more preferably from 0.1–0.7 wt. % and even more preferably from 0.12–0.55 wt. %.

Other antioxidants, such as ascorbic acid, acetylcysteine, cysteine, sodium hydrogen sulfite, butyl-hydroxyanisole, and alpha-tocopherol acetate may be present too.

An advantage of an antioxidant comprised in a polymeric material in accordance to the present invention is that there is typically only a minimal release or substantially no release of said antioxidant into a pharmaceutical and in particular into an aqueous ophthalmic composition which composition is in contact with said polymeric material. This may typically result in a substantial exclusion of said antioxidant from said pharmaceutical composition.

An antioxidant is typically used during the manufacturing process of a polymeric material in order to avoid decomposition and/or oxidation. Consequently, such a polymer is in particular within the terms of the present invention, namely a polymeric material comprising an antioxidant.

A pharmaceutical active ingredient is e.g. selected from the group consisting of acetylcholine chloride, acyclovir, adrenaline, amethocaine, aminocaproic acid, antazoline phosphate, arachidonic acid, atropine, betaxolol, bupivacaine, carbachol, carteolol, chloramphenicol, chlortetracycline, chymatrypsin, clonidine, cocaine, corynanthine, cromolyn, cyclopentolate, demecarium, dexamethasone, dibutoline, dichlorphenamide, diclofenac, dipivefrin, echodtiophate, ephedrine, erythromycin, ethambutol, etidocaine, eucatropine, fluoromethalone, fluorometholone, gentamycin, gramicidine, H-thymidine, homatropine, hyaluronic acid, hydrocortisone, idoxuridine, indomethacin, isoflurophate, isosorbide, ketorolac, ketotifen, lachesine, levobunolol, levocabastine, lidocaine, lignocaine, medrysone, mepivacaine, methacholine, methazolamide, naphazoline, natamycin, neomycin, neostigmine, noradrenaline, ofloxacin, oxybuprocaine, oxymetazolin, oxyphenonium, pheniramine, phenylephrine, physostigmine, pilocarpine, polymyxin B, prednisolone, proparacaine, proxymethacaine, pyrilamine, retinoic acid, retinol, retinol acetate, retinol palmitate, scopolamine, sorbinil, sulfacetamide, tamoxifen, tetracaine, tetracycline, tetrahydrozoline, timolol, trifluridine, tropicamide, vidarabine, and pharmaceutically acceptable salts, and mixtures thereof.

Preferred pharmaceutically active compounds are selected from the group of betaxolol, chloramphenicol, diclofenac, dipivefrin, ephedrine, erythromycin, gentamycin, indomethacin, ketotifen, levobunolol, levocabastine, ofloxacin, pilocarpine, polymyxin B, prednisolone, retinoic acid, retinol, retinol acetate, retinol palmitate, tetracycline and pharmaceutically acceptable salts thereof.

More preferred pharmaceutically active compounds are selected from the group of, betaxolol, chloramphenicol, diclofenac, ketotifen, levobunolol, levocabastine, pilocarpine, retinoic acid, retinol, retinol acetate, retinol palmitate and pharmaceutically acceptable salts thereof.

Highly preferred is ketotifen, retinoic acid, retinol, retinol acetate, retinol palmitate and pharmaceutically acceptable salts thereof.

Very particular preferred is ketotifen and pharmaceutically acceptable salts thereof.

Within the present invention a pharmaceutical composition is characterized by the carrier wherein said pharmaceutical active compound is mixed, suspended, dissolved and/or partially dissolved and is selected from the group consisting of water, mixtures of water and water-miscible solvents, such as $C_1$- to $C_7$-alkanols, vegetable oils or mineral oils comprising from 0.5 to 5% by weight hydroxyethyicellulose, ethyl oleate, carboxymethylcellulose, polyvinyl-pyrrolidone and other non-toxic water-soluble polymers, in particular for ophthalmic uses, such as, for example, cellulose derivatives, such as methylcellulose, alkali metal salts of carboxy-methylcellulose, hydroxymethylcellulose, hydroxyethylcellulose, methylhydroxypropyl-cellulose and hydroxypropylcellulose, acrylates or methacrylates, such as salts of polyacrylic acid or ethyl acrylate, polyacrylamides, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers. Preferred carriers are water, cellulose derivatives, such as methylcellulose, alkali metal salts of carboxymethylcellulose, hydroxymethylcellulose, hydroxyethylcellulose, methylhydroxy-propylcellulose and hydroxypropylcellulose, neutral Carbopol, or mixtures thereof. A highly preferred carrier is water. The concentration of the carrier is, typically, from 1 to 100000 times the concentration of the active ingredient. The term aqueous typically denotes an aqueous composition wherein the carrier is to an extent of >50%, more preferably >75% and in particular >90% by weight water.

Within the terms of the present invention the term composition relates in particular to a solution, a suspension, a gel, an ointment, an emulsion and/or a mixture thereof.

Further preference is given to pharmaceutical compositions which are suitable for ocular administration. Therefore such a pharmaceutical composition preferably comprises further ingredients in order to meet the prerequisites for ocular tolerability. In a particular aspect, the present invention relates therefore to the stabilization of an ophthalmic composition and in particular to an aqueous ophthalmic composition.

These further ingredients may include tonicity enhancers, preservatives and pH adjusting agents.

For the adjustment of the pH, preferably to a physiological pH, buffers may especially be useful. Examples of buffer substances are acetate, ascorbate, borate, hydrogen carbonate/carbonate, citrate, gluconate, lactate, phosphate, propionate and TRIS (tromethamine) buffers. Tromethamine and borate buffer are preferred buffers. The amount of buffer substance added is, typically, that necessary to ensure and maintain a physiologically tolerable pH range. The pH range is generally in the range of from 4 to 9, preferably from 4.5 to 8.5 and more preferably from 5.0 to 8.2.

Tonicity is adjusted if needed typically by tonicity enhancing agents. Such agents may, for example be of ionic and/or non-ionic type. Examples of ionic tonicity enhancers are e.g. alkali metal or earth metal halides, such as, for example, $CaCl_2$, KBr, KCl, LiCl, NaI, NaBr or NaCl, $Na_2SO_4$ or boric acid. Non-ionic tonicity enhancing agents are, for example, urea, glycerol, sorbitol, mannitol, propylene glycol, or dextrose. Typically, a sufficient amount of tonicity enhancing agent may be added to impart to an above ophthalmic composition an osmolality of approximately from 50 to 1000 mOsmol, preferred from 100 to 400 mOsmol, more preferred from 200 to 400 mOsmol and even more preferred from 250 to 350 mOsmol.

A preservative may typically be selected from a quaternary ammonium compound such as benzalkonium chloride, benzoxonium chloride or the like. Benzalkonium chloride is better described as: N-benzyl-N-($C_8$–$C_{18}$alkyl)-N,N-dimethylammonium chloride. Examples of preservatives different from quaternary ammonium salts are alkyl-mercury salts of thiosalicylic acid, such as, for example, thiomersal, phenylmercuric nitrate, phenylmercuric acetate or phenylmercuric borate, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, sodium perborate, Germal®II or sorbic acid. Preferred preservatives are quaternary ammonium compounds, in particular benzalkonium chloride, alkyl-mercury salts and parabens. Where appropriate, a sufficient amount of preservative is added to the ophthalmic composition to ensure protection against secondary contaminations during use caused by bacteria and fungi.

A pharmaceutical composition may additionally require the presence of a solubilizer, in particular if the active or the inactive ingredients tends to form a suspension or an emulsion. A solubilizer suitable for an above concerned composition is for example selected from the group consisting of tyloxapol, fatty acid glycerol polyethylene glycol esters, fatty acid polyethylene glycol esters, polyethylene glycols, glycerol ethers, a cyclodextrin (for example α-, β- or γ-cyclodextrin, e.g. alkylated, hydroxyalkylated, carboxyalkylated or alkyloxycarbonyl-alkylated derivatives, or mono- or diglycosyl-α-, β- or γ-cyclodextrin, mono- or dimaltosyl-α-, β- or γ-cyclodextrin or panosyl-cyclodextrin), polysorbate 20, polysorbate 80 or mixtures of those compounds. A specific example of an especially preferred solubilizer is a reaction product of castor oil and ethylene oxide, for example the commercial products Cremophor EL® or Cremophor RH 40®. Reaction products of castor oil and ethylene oxide have proved to be particularly good solubilizers that are tolerated extremely well by the eye. Another preferred solubilizer is selected from tyloxapol and from a cyclodextrin. The concentration used depends especially on the concentration of the active ingredient. The amount added is typically sufficient to solubilize the active ingredient. For example, the concentration of the solubilizer is from 0.1 to 5000 times the concentration of the active ingredient.

An above pharmaceutical composition may comprise further non-toxic excipients, such as, for example, emulsifiers, wetting agents or fillers, such as, for example, the polyethylene glycols designated 200, 300, 400 and 600, or Carbowax designated 1000, 1500, 4000, 6000 and 10000. Other excipients that may be used if desired are listed below but they are not intended to limit in any way the scope of the possible excipients. The amount and type of excipient added is in accordance with the particular requirements and is generally in the range of from approximately 0.0001 to approximately 90% by weight.

Further objects of the present invention are those disclosed in all dependent and independent claims.

A further object of the present invention is the use of a plastic bottle in accordance to the examples for stabilizing a composition disclosed therein.

| Example 1: Ketotifen 0.025% Eye Drops | | |
|---|---|---|
| | in 10 ml PE-bottles (no antioxidant) | in 10 ml PP-bottles (+ Irganox 1330) |
| 0-Value | | |
| Content of ketotifen hydrogen fumarate in % | 97.7 | 97.7 |
| pH | 5.06 | 5.06 |
| Osmolality (mOsmol) | 247 | 247 |

-continued

Example 1: Ketotifen 0.025% Eye Drops

| | in 10 ml PE-bottles (no antioxidant) | in 10 ml PP-bottles (+ Irganox 1330) |
|---|---|---|
| Stresstest, 15 hrs, 80° C. | | |
| Content of ketotifen hydrogen fumarate in % | 73.7 | 96.2 |
| Known degradation products in % | 2.6 | 0.04 |
| pH | 4.42 | 4.96 |
| Osmolality (mOsmol) | 247 | 248 |

Example 2: Ketotifen 0.05% Eye Drops

| | 10 ml PE-bottles (white) (no antioxidant) | 10 ml PP-bottles (white) (+ Irganox 1330) |
|---|---|---|
| 0 Value | | |
| Content of ketotifen hydrogen fumarate in % | 97.8 | 97.8 |
| pH | 5.30 | 5.30 |
| Osmolality (mOsmol) | 248 | 248 |
| 3 month, 25° C. | | |
| Content of ketotifen hydrogen fumarate in % | 96.0 | 99.2 |
| Known degradation products in % | 0.6 | not detectable |
| Unknown degradation products in % | not determinable | not detectable |
| pH | 5.0 | 5.64 |
| 3 month, 30° C. | | |
| Content of ketotifen hydrogen fumarate in % | 93.5 | 99.2 |
| Known degradation products in % | 1.6 | not detectable |
| Unknown degradation products in % | 0.5 | not detectable |
| pH | 4.93 | 5.62 |
| 3 month, 40° C. (20% relative humidity) | | |
| Content of ketotifen hydrogen fumarate in % | 79.2 | 99.8 |
| Known degradation products in % | 7.5 | not determinable |
| Unknown degradation products in % | 3.2 | not detectable |
| pH | 4.57 | 5.35 |
| 3 month, 40° C. (75% relative humidity) | | |
| Content of ketotifen hydrogen fumarate in % | 83.4 | 99.4 |
| Known degradation products in % | 4.3 | not detectable |
| Unknown degradation products in % | 1.6 | not detectable |
| pH | 4.66 | 5.55 |

Example 3: Ingredients comprised in a 0.025% ophthalmic composition comprising ketotifen:

| Names of ingredients | (mg/ml) | Function | Reference to standards |
|---|---|---|---|
| Active ingredient | | | |
| Ketotifen (used as Ketotifen hydrogen fumarate) | 0.25 (0.345) | antiallergic agent | |
| Other ingredients | | | |
| Benzalkonium chloride | 0.10 | preservative | Ph. Eur. |
| Glycerol | 21.25 | isotonizing agent | Ph. Eur. |
| 1 M Sodium hydroxide | ~0.75 (to a pH of about 5.3) | pH adjusting agent | Ph. Eur. |
| Water for injections | ~981.055 (ad 1.0 ml) | solvent | Ph. Eur. |

Example 4: Ingredients comprised in a 0.05% ophthalmic composition comprising ketotifen:

| Names of ingredients | Formula (mg/ml) | Function | Reference to standards |
|---|---|---|---|
| Active ingredient | | | |
| Ketotifen (used as Ketotifen hydrogen fumarate) | 0.50 (0.69) | antiallergic agent | |
| Other ingredients | | | |
| Benzalkonium chloride | 0.10 | preservative | Ph. Eur. |
| Glycerol 85% | 25.00 | tonicity adjusting agent | Ph. Eur. |
| Sodium hydroxide 1 N | ~1.50 (to a pH of about 5.3) | pH adjusting agent | Ph. Eur. |
| Water for injections | ~976.21 (ad 1.0 ml) | solvent | Ph. Eur. |

Example 5: Vitamin A eye drops

| | 5 ml PE-bottles without antioxidant | 5 ml PP-bottles with Irganox 1330 |
|---|---|---|
| 0-Value | | |
| Content of Vit. A palmitate in IU | 1272 | 1272 |
| pH | 6.67 | 6.67 |
| Osmolality (mOsmol) | 310 | 310 |
| 40° C., 1 month, 75% relative humidity | | |
| Content of Vit. A palmitate in IU | 1097 | 1204 |
| pH | 6.67 | 6.67 |
| Osmolality (mOsmol) | 310 | 3.10 |

Example 6:
Ingredients comprised in Vitamin A eye drops (gel)

| compound | mg/ml | function | reference to standards |
|---|---|---|---|
| synthetic vitamin A palmitate, water dispersible form (100'000 IU/g) | 10 (1000 IU) | antixeroph-thalmic | Ph. Eur. |
| benzalkonium chloride | 0.10 | preservative | Ph. Eur. |
| α-tocopherol acetate, water dispersible form (0.5 g/g) | 10.0 | antioxidant | |
| boric acid | 16.20 | buffer | Ph. Eur. |
| borax | 1.40 | buffer | Ph. Eur. |
| disodium edetate | 1.00 | chelating agent | Ph. Eur. |
| methylhydroxypropylcellulose | 4.00 | viscosity enhancer | Ph. Eur. |
| water for injections | ad 1.0 ml | carrier (solvent) | Ph. Eur. |

Ph. Eur. = European Pharmacopoeia
IU = International Units

Example 7
Ketotifen eye drops of example 3 (0.025% ophthalmic composition) exposed to stability test:

| Composition (mg/ml) | Batch-7A filled into PP-bottles containing Irganox 1330, | Batch-7B filled into PP-bottles containing Irganox 1330, autoclaved before filling | Batch-7C PP-bottles containing BHT, sterilised with ethylene oxide before filling |
|---|---|---|---|
| ketotifen hydrogen fumarate | 0.345 | identical to 7A | identical to 7A |
| benzalkonium chloride | 0.10 | identical to 7A | identical to 7A |
| glycerol | 21.25 | identical to 7A | identical to 7A |
| 1 M sodium hydroxide | ~0.75 | identical to 7A | identical to 7A |
| Water for injection | ~981.055 | identical to 7A | identical to 7A |
| | 0-Value | | |
| Content of ketotifen hydrogen fumarate in % | 96.5 | 100.0 | 99.6 |
| pH | 5.12 | 5.38 | 5.55 |
| osmolality (mOsmol) | 241 | 238 | 238 |
| stress test at 40° C. and 75% relative humidity | | | |
| | 12 months | 3 months | 3 months |
| Content of ketotifen hydrogen fumarate in % | 99.9 | 99.2 | 98.2 |

Example 7
Ketotifen eye drops of example 3 (0.025% ophthalmic composition) exposed to stability test:

| Composition (mg/ml) | Batch-7A filled into PP-bottles containing Irganox 1330, | Batch-7B filled into PP-bottles containing Irganox 1330, autoclaved before filling | Batch-7C PP-bottles containing BHT, sterilised with ethylene oxide before filling |
|---|---|---|---|
| degradation products in % | ~2.08 | <0.1 | <0.05 |
| pH | 5.16 | 5.35 | 5.56 |
| Osmolality (mOsmol) | 244 | 240 | 242 |

BHT: butylhydroxytoluene

What is claimed is:

1. A composition comprising (a) an aqueous component comprising a solution of water and ketotifen fumarate and (b) a polymeric component comprising an antioxidant and polypropylene, wherein said aqueous component and said polymeric component are in contact in said composition.

2. A composition of claim 1, wherein said aqueous component further comprises glycerol.

3. A composition of claim 2, wherein said aqueous component further comprises benzalkonium chloride.

4. A composition of claim 1, comprising (a) an aqueous component comprising a solution of water, ketotifen fumarate, glycerol, and benzalkonium chloride and (b) a polymeric component comprising an antioxidant and polypropylene, wherein said aqueous component and said polymeric component are in contact in said composition.

5. A composition of claim 4, wherein said antioxidant is butylhydroxytoluene.

6. A composition of claim 4, comprising (a) an aqueous component comprising a solution of water, 0.0345% ketotifen fumarate by weight, 2.125% glycerol by weight, and benzalkonium chloride 0.01% by weight and (b) a polymeric component comprising an antioxidant and polypropylene, wherein said aqueous component and said polymeric component are in contact in said composition.

7. A composition of claim 6, wherein the pH of said solution is about 5.3.

8. A composition of claim 6, wherein said antioxidant is butylhydroxytoluene.

9. A composition of claim 8, wherein the pH of said solution is about 5.3.

* * * * *

UNITED STATES PATENT AND TRADEMARK OFFICE
CERTIFICATE OF CORRECTION

PATENT NO.     : 6,455,547 B1
DATED          : September 24, 2002
INVENTOR(S)    : Gyorgy Lajos Kis It is certified that error appears in the above-identified patent and that said Letters Patent is hereby corrected as shown below:

<u>Title page,</u>
Item [63], Related U.S. Application Data, should read:
-- Continuation of application No. 09/627,799, filed on Jul. 28, 2000, which is a continuation of application No. PCT/EP99/02221, filed on March 31, 1999. --

Signed and Sealed this

Eighteenth Day of February, 2003

JAMES E. ROGAN
*Director of the United States Patent and Trademark Office*